United States Patent [19]

Peterson et al.

[11] Patent Number: 5,780,020
[45] Date of Patent: Jul. 14, 1998

[54] METHODS AND COMPOSITIONS FOR REDUCING BODY ODOR

[75] Inventors: Liezl Gonzales Peterson, Loveland, Ohio; Patricia Alison LaFleur, Shrewsbury, Pa.

[73] Assignee: The Proctor & Gamble Company, Cincinnati, Ohio

[21] Appl. No.: 736,838

[22] Filed: Oct. 28, 1996

[51] Int. Cl.$^6$ .............................. A61K 7/32; A61K 7/36
[52] U.S. Cl. .............................. 424/65; 424/67; 424/69; 424/78.03; 424/401; 424/405; 424/642; 424/715; 424/717; 422/5
[58] Field of Search .............................. 424/65, 67, 69, 424/78.03, 401, 405, 642, 715, 717; 422/5

[56] References Cited

U.S. PATENT DOCUMENTS

| | | | |
|---|---|---|---|
| 3,081,223 | 3/1963 | Gunning et al. | 167/39 |
| 3,172,817 | 3/1965 | Leupold et al. | 167/90 |
| 3,426,011 | 2/1969 | Parmerter et al. | |
| 3,453,257 | 7/1969 | Parmerter et al. | |
| 3,453,258 | 7/1969 | Parmerter et al. | |
| 3,453,259 | 7/1969 | Parmerter et al. | |
| 3,453,260 | 7/1969 | Parmerter et al. | |
| 3,459,731 | 8/1969 | Gramera et al. | |
| 3,553,191 | 1/1971 | Parmerter et al. | |
| 3,565,887 | 2/1971 | Parmerter et al. | |
| 3,574,821 | 4/1971 | Pfirrmann et al. | 424/45 |
| 4,014,995 | 3/1977 | Juliano et al. | 424/168 |
| 4,078,051 | 3/1978 | Pomot et al. | 424/35 |
| 4,272,514 | 6/1981 | Spence | 424/69 |
| 4,278,658 | 7/1981 | Hooper et al. | 424/65 |
| 4,352,794 | 10/1982 | Koch | 424/180 |
| 4,382,079 | 5/1983 | Marschner | 424/65 |
| 4,407,789 | 10/1983 | Eigen et al. | 424/69 |
| 4,535,152 | 8/1985 | Szejtli et al. | 536/103 |
| 4,556,560 | 12/1985 | Buckingham | 424/145 |
| 4,616,008 | 10/1986 | Hirai et al. | 514/200 |
| 4,650,670 | 3/1987 | Callingham et al. | 424/65 |
| 4,659,564 | 4/1987 | Cox et al. | 424/65 |
| 4,664,910 | 5/1987 | Caserio et al. | 424/70 |
| 4,678,598 | 7/1987 | Ogino et al. | 252/174.17 |
| 4,727,824 | 3/1988 | Ducharme et al. | 119/1 |
| 4,743,440 | 5/1988 | Callingham et al. | 424/46 |
| 4,746,734 | 5/1988 | Tsuchiyama et al. | 536/103 |
| 4,788,060 | 11/1988 | Endicott et al. | 424/443 |
| 4,837,011 | 6/1989 | Macchio et al. | 424/69 |
| 4,881,490 | 11/1989 | Ducharme et al. | 119/1 |
| 4,883,021 | 11/1989 | Ducharme et al. | 119/1 |
| 4,904,524 | 2/1990 | Yoh | 428/311.3 |
| 4,913,896 | 4/1990 | Harvey | 424/69 |
| 5,010,109 | 4/1991 | Inoi | 514/714 |
| 5,098,693 | 3/1992 | Faas, Jr. et al. | 424/45 |
| 5,152,983 | 10/1992 | Nambudiry et al. | 424/60 |
| 5,306,487 | 4/1994 | Karapasha et al. | 424/76.6 |
| 5,370,875 | 12/1994 | Rogozinski | 424/405 |
| 5,429,628 | 7/1995 | Trinh et al. | 604/359 |
| 5,453,266 | 9/1995 | Malka | 424/65 |
| 5,486,355 | 1/1996 | Berschied, Jr. | 424/65 |
| 5,508,028 | 4/1996 | Berschied, Jr. | 424/65 |
| 5,512,199 | 4/1996 | Khan et al. | 252/106 |
| 5,518,727 | 5/1996 | Lajoie et al. | 424/400 |
| 5,525,331 | 6/1996 | Betts | 424/65 |
| 5,534,165 | 7/1996 | Pilosof et al. | 252/8.91 |
| 5,540,853 | 7/1996 | Trinh et al. | 510/101 |
| 5,543,157 | 8/1996 | Trinh et al. | 424/493 |
| 5,552,378 | 9/1996 | Trinh et al. | 512/3 |
| 5,580,851 | 12/1996 | Trinh et al. | 512/4 |

FOREIGN PATENT DOCUMENTS

| | | |
|---|---|---|
| 0701812 A1 | 3/1996 | European Pat. Off. |
| 2201880 | 5/1974 | France . |
| 87637 | 11/1972 | Germany . |
| 2304156 A | 8/1974 | Germany . |
| 2731520 | 1/1979 | Germany . |
| 229304 A1 | 11/1985 | Germany . |
| SHO 53-41440 | 4/1978 | Japan . |
| SHO 58-124452 | 7/1983 | Japan . |
| SHO 61-128973 | 6/1986 | Japan . |
| 63-164953 | 7/1988 | Japan . |
| HEI 3-170415 | 7/1991 | Japan . |
| HEI 3-284616 | 12/1991 | Japan . |
| 5-269185 | 10/1993 | Japan . |
| 7-100644 | 11/1995 | Japan . |
| 1472536 | 5/1977 | United Kingdom . |
| WO 91/12029 | 8/1991 | WIPO . |
| WO 94/22500 | 10/1994 | WIPO . |
| WO 96/04937 | 2/1996 | WIPO . |
| WO 96/04938 | 2/1996 | WIPO . |
| WO 96/04940 | 2/1996 | WIPO . |
| WO 96/05358 | 2/1996 | WIPO . |

OTHER PUBLICATIONS

Furuta, T., et al., "Effects of Water and Alcohol on the Formation of Inclusion Complexes of d–limonene and Cyclodextrins", Supramolecular Chemistry, vol. 1 (1993), pp. 321–325.

Furuta, T., et al., "Formation of Inclusion Complex Between Cyclodextrin and d–limonene by a Twin Screw Kneader", The 7th International Cyclodextrins Symposium, Tokyo, Japan (Apr. 25–28, 1994), pp. 512–515.

Hashimoto, H., "Studies on the Industrial Production and Application of Cyclodextrins", Starch Science, vol. 36, No. 1 (1989), pp. 35–42.

(List continued on next page.)

*Primary Examiner*—Nathan M. Nutter
*Attorney, Agent, or Firm*—Mary Catherine Hentz; Douglas C. Mohl; Jacobus C. Rasser

[57] ABSTRACT

The present invention relates to a powder, odor absorbing composition, which is safe for use on human skin comprising from about 0.1% to about 25%, by weight of the composition, of uncomplexed cyclodextrin; and a powder carrier. The odor absorbing compositions of the present invention may also contain an additional odor controlling agent, selected from the group consisting of zeolites, activated charcoal, sodium bicarbonate, antimicrobial agents, and antiperspirants.

The present invention also relates to methods of using the compositions of the present invention to reduce body odor and/or vaginal odor.

16 Claims, No Drawings

OTHER PUBLICATIONS

Hashimoto, H., "Application of Cyclodextrins to Foods, Toiletries and Other Products in Japan", Ensuiko Sugar Refining Co., Ltd., pp. 13–46, 1988.

Lehner, S. J., et al., "Interactions Between p-hydroxybenzoic Acid Esters and Hydroxypropyl-β-Cyclodextrin and Their Antimicrobial Effect Against *Candida Albicans*", International Journal of Pharmaceuticals, 93 (1993), pp. 201–208.

Djedaini-Pilard, F., et al., "Optimal Performances with Minimal Chemical Modifcations of Cyclodextrins", The 7th International Cyclodextrins Symposium, Tokyo, Japan (Apr. 25–28, 1994), pp. 94–97.

Leyden, "Bacteriology of the Human Axilla: Relationship to Axillary Odor", Antiperspirants & Deodorants, 1988, pp. 311–319.

"Skin Products for Babies", Harry's Cosmeticology, 1982, pp. 112–113; 288–297; 300–304; 757–761; 764–765.

Lachman, et al., The Theory and Practice of Industrial Pharmacy, 1986, pp. 466–467; 520–522; 458–461.

U.S. application No. 08/889,607, Trinh et al., filed Jul. 8, 1997.

U.S. application No. 08/871,166, Lucas et al., filed Jun. 9, 1997.

U.S. application No. 08/871,854, Lucas et al., filed Jun. 9, 1997.

U.S. application No. 08/871,791, Dodd et al., filed Jun. 9, 1997.

U.S. application No. 08/871,855, Trinh et al., filed Jun. 9, 1997.

U.S. application No. 08/871,853, Lucas et al., filed Jun. 9, 1997.

U.S. application No. 08/871,857, Lucas et al., filed Jun. 9, 1997.

U.S. application No. 08/871,790, Peterson et al., filed Jun. 9, 1997.

U.S. application No. 08/871,856, Peterson et al., filed Jun. 9, 1997.

U.S. application No. 08/871,858, Lucas et al., filed Jun. 9, 1997.

U.S. application No. 08/871,577, Lucas et al., filed Jun. 9, 1997.

U.S. application No. 08/871,860, Lucas et al., filed Jun. 9, 1997.

U.S. application No. 08/871,861, Peterson et al., filed Jun. 9, 1997.

U.S. application No. 08/871,092, Peterson et al., filed Jun. 9, 1997.

U.S. application No. 08/289,732, Trinh et al., filed Aug. 12, 1994.

U.S. application No. 08/289,733, Trinh et al., filed Aug. 12, 1994.

U.S. application No. 08/289,734, Cappel et al., filed Aug. 12, 1994.

U.S. application No. 08/289,735, Cappel et al., filed Aug. 12, 1994.

U.S. application No. 08/289,969, Pilosof et al., filed Aug. 12, 1994.

U.S. application No. 08/871,576, Woo et al., filed Jun. 9, 1997.

U.S. application No. 08/871/119, Woo et al., filed Jun. 9, 1997.

U.S. application No. 08/871,042, Woo et al., filed Jun. 9, 1997.

METHODS AND COMPOSITIONS FOR REDUCING BODY ODOR

BACKGROUND OF THE INVENTION

The human skin is naturally populated with numerous micro-organisms. These organisms are nourished by various skin secreted substances, skin cell debris, breakdown products of the skin and the organisms themselves. The "skin secretions" are eccrine and apocrine sweat, and lipid-soluble sebum. Eccrine sweat is normally odorless and remains odorless after secretion, although odoriferous food and drug substances may be excreted with it. Apocrine glands are normally associated with hair follicles and are confined mainly to the groin, perianal, areola and armpits. They produce a scanty, milky substance that is odorless upon secretion, but becomes odoriferous upon bacterial decomposition. Apocrine glands are considered to be a primary contributor for malodor. The sebaceous glands are distributed over the skin surface except the palms and dorsae. They are most numerous on the scalp, forehead, face, back and chest. The secretion, sebum, consists mainly of fatty materials, wax esters, cholesterol and its esters and squalene. Sebum is typically associated with acne.

Specifically, body odor is most commonly caused by fatty acids on skin and from malodors from bacterial sources. The unpleasant odors are mainly organic molecules which have different structures and functional groups, such as amines, acids, alcohols, aldehydes, ketones, phenolics, polycyclics, indoles, aromatics, polyaromatics, etc. They can also be made up of sulfur-containing functional groups, such as, thiol, mercaptan, sulfide and/or disulfide groups.

Numerous attempts have been made to conceal body odors through the use of perfumes. Not only are such perfumes often inadequate at fully concealing the body odors, very often they are irritating to the user's skin. Additionally, the perfume odor itself may be irritating or offensive to the user's respiratory system and/or olfactory senses, as well as to nearby individuals.

Other attempts have been made to control odor through moisture absorption. Odor causing bacteria and fungi often flourish in warm, moist conditions; particularly where they have easy access to nourishment such as skin secretions and skin cell debris. Therefore, attempts are made to deprive the bacteria responsible for body odor of the moist/humid environment they need to proliferate and grow. Such efforts include the use of powders and/or antiperspirants. Powders and powder-based compositions of the prior art may be difficult to apply and have limited absorption capabilities. Therefore, use of the body powders of the prior art is undesirable and/or ineffective for day to day body odor control for the entire body. Antiperspirants are not useful in a body odor control product for use over the entire body as they may interfere with the body's thermal regulatory process by inhibiting perspiration through the action of astringent salts. Additionally, such salts may be irritating to a large number of users, particularly when applying them to sensitive areas such as the pelvic region.

Numerous other deodorant compositions aimed at combating odor associated with the skin secretions have been described in the chemical and cosmetic literature. These generally are emulsion sticks or suspensoid sticks, but also may be aerosols, roll-ons, pads, pump sprays, and even soap bars.

Known deodorants attempt to control odor through a variety of means. Deodorants may include antibacterial compounds which help destroy and/or control the amount of bacteria present on the skin, thereby minimizing odor produced via bacterial metabolism of the skin secretions. U.S. Pat. No. 5,525,331, to Betts, issued Jun. 11, 1996, discloses compositions which inhibit the growth of micro-organisms in the body-secretions. Yet another attempt at controlling body odor is found in U.S. Pat. No. 4,382,079, to Marschner, issued May 3, 1983, which discloses the use of sodium bicarbonate as an underarm deodorant to neutralize offending body odor.

Zeolites such as those marketed under the trade name ABSCENTS by the Union Carbide Corporation and UOP are known odor absorbers. However these commonly known solid odor absorbers, in addition to known activated charcoal odor absorbers, lose functionality when wet. Therefore, when wetted by body fluids or when carried in an aqueous solution, these odor absorbers are not preferred as they lose their desired odor absorbent characteristics. Furthermore, zeolites can cause a "harsh" feel if too much is deposited onto the skin.

Thus, there remains a need for an improved odor absorbing composition, which is essentially free of irritating ingredients such as perfumes and which is safe and effective for use on the entire body. More particularly, there is a need for a convenient composition which is left on the skin and is capable of absorbing a broad spectrum of body odors that are not filly suppressed by the aforementioned means.

It has been discovered that such enhanced body odor control can be safely provided to the entire body by applying a composition, which is left on the skin, which incorporates odor absorbing, uncomplexed cyclodextrins and a powder carrier. It has been discovered that a particular advantage of the present invention is the ability to provide convenient, non-irritating odor protection when applied to occluded skin areas such as the pelvic region, the external vagina, the panty-area, the bra-line, and skin-folds, which may be very sensitive. Moreover, it has been discovered that the aforementioned benefits may be delivered in a powder carrier which also optionally delivers skin aid benefits to the user such as protection and/or moisturization.

These and other objects of the present invention will become readily apparent from the detailed description which follows.

All percentages, ratios, and parts herein, in the Specification, Examples, and claims are by weight unless otherwise stated. The term "g", as used herein, means gram. The term "ml", as used herein, means milliliter.

SUMMARY OF THE INVENTION

The present invention relates to a powder, odor absorbing composition, which is safe for use on human skin comprising from about 0.1% to about 25%, by weight of the composition, of uncomplexed cyclodextrin; and a powder carrier. The odor absorbing compositions of the present invention may also contain an additional odor controlling agent, selected from the group consisting of zeolites, activated charcoal, sodium bicarbonate, antimicrobial agents, and antiperspirants.

The present invention also relates to methods of using the compositions of the present invention to reduce body odor and/or vaginal odor.

DETAILED DESCRIPTION OF THE INVENTION

The present invention relates to a perfume-free, powder, odor-absorbing composition. The present invention also relates to a method of reducing body odor comprising the application of a perfume-free odor-absorbing composition. The composition can be applied to skin directly as a spray, shaken from a bottle or canister and applied by hand, or applied via wipe which is dry.

The composition of the present invention comprises dry ingredients preferably having particle sizes of from about 1 micron to about 100 microns; more preferred from about 1 micron to about 60 microns; and most preferred from about 1 micron to about 20 microns. As used herein, the particle size refers to the largest dimension of the particle and to the ultimate (or primary) particles.

The term "occluded skin", as used herein, refers to regions of a human body covered by undergarments, such as the pelvic area, panty-area, and bra-line; and skin-folds or intertriginous regions, where there is continuing skin to skin contact.

The term "excess moisture", as used herein, means an undesirable and/or unhealthy level of body fluids deposited on the human skin.

The term "body fluids", as used herein, includes eccrine sweat, apocrine sweat, sebum, build up of sensible moisture from transepidermal water loss, vaginal discharge, urine, and mixtures thereof.

The term "body odor" as used herein means odors which are generated as a result of the natural functioning of a human body. Such odors include, but are not limited to odors produced by microorganisms of the human skin (i.e. bacterial decomposition of skin secretions), urine, or vaginal discharge, and mixtures thereof.

The term "entire body" means the entire external surface of human or mammalian skin.

The term "vaginal odor" relates specifically to those body odors which emanate from the pelvic region of a woman, particularly the vagina and the panty line.

A detailed description of essential and optional components of the present invention is given below.

Cyclodextrin

As used herein, the term "cyclodextrin" includes any of the known cyclodextrins such as unsubstituted cyclodextrins containing from six to twelve glucose units, especially alpha-cyclodextrin, beta-cyclodextrin, gamma-cyclodextrin and/or their derivatives and/or mixtures thereof.

The term "uncomplexed cyclodextrin" as used herein means that the cavities within the cyclodextrin in the composition of the present invention should remain essentially unfilled prior to application to skin in order to allow the cyclodextrin to absorb various odor molecules when the composition is applied to the skin.

Preferred cyclodextrins for use in the present invention are alpha-cyclodextrin, beta-cyclodextrin, gamma-cyclodextrin and/or their derivatives. More preferred are beta cyclodextrin, hydroxypropyl alpha-cyclodextrin, hydroxypropyl beta-cyclodextrin, methylated-alpha-cyclodextrin or methylated-beta-cyclodextrin. Most preferred is beta-cyclodextrin.

It is also preferable to use a mixture of cyclodextrins. Such mixtures absorb body odors more broadly by complexing with a wider range of odoriferous molecules having a wider range of molecular sizes. The levels of cyclodextrin are from about 0.1% to about 25%, preferably from about 1% to about 20%, more preferably from about 2% to about 15%, most preferably from about 3% to about 10%, by weight of the composition.

The complexation between cyclodextrin and odorous molecules occurs rapidly when wetted with body fluids. This is convenient for the user because the cyclodextrins, while on dry skin, will not fill their cavities with other environmental odors which would otherwise render them less efficient for absorbing body odors. More particularly, upon solubilization of the cyclodextrins by the body fluids, the isolated cavities become available to form inclusion complexes with the body odor molecules. Thus, ultimately, the availability of solubilized uncomplexed cyclodextrin is essential for an effective and efficient odor control performance.

Cyclodextrins having small particle sizes aid in providing higher cyclodextrin surface availability for odor absorption and therefore are preferred. As used herein, the particle size refers to the largest dimension of the particle and to the ultimate (or primary) particles. Small particle cyclodexrins of this invention are those having a particle size of less than about 12 microns, preferably less than about 10 microns, and more preferably less than about 5 microns. A more complete description of the cyclodextrins, cyclodextrin derivatives, and cyclodextrin particle sizes useful in the present invention can be found in U.S. Pat. No. 5,429,628, Trinh et al., issued Jul. 4, 1995, which is incorporated herein by reference in its entirety.

Powder Carrier

The cyclodextrins useful in the present invention should be dispersed in a pharmaceutically-acceptable powder carrier for convenient, uniform application and disbursement onto the skin. The term "pharmaceutically-acceptable", as used herein, means a powder suitable for topical use on the skin without undue toxicity, irritation, allergic response, and the like. The powder carrier also helps prevent any solubilized cyclodextrin from washing away from the desired skin contact. Powder carriers useful in the present invention include powders known in the art to be safe for human skin. Such powders include but are not limited to cornstarch (topical starch), talc, rice starch, oat starch, tapioca starch, microcrystalline cellulose (for example Avicel®), aluminum starch octenyl succinate (sold by National Starch & Chemical Co. as Dry Flo® Pure, Dry Flo® XT, and/or Dry Flo® PC), kaolin, and mixtures thereof. Preferred is cornstarch.

The powder carrier of the present invention will comprise from about 10% to about 99%, preferably from about 15% to about 80%, more preferably from about 25% to about 50%, by weight of the composition.

Adjunct Odor Controlling Agents

Optionally, the compositions of the present invention may comprise zeolites, carbon odor-controlling agents, sodium bicarbonates, antimicrobial agents and/or antiperspirant ingredients for added body odor control.

The term "zeolite", as used herein, refers to non-fibrous zeolites. When included in the present invention, zeolites may be present from about 0.1% to about 25%, preferably from about 1% to about 15%, by weight of the composition. A detailed description of zeolites useful in the present invention is found in U.S. Pat. No. 5,429,628, Trinh et al., issued Jul. 4, 1995, incorporated herein by reference in its entirety.

Carbon odor-controlling agents described in U.S. Pat. No. 5,429,628 may be used in the present invention at a level of from about 0.1% to about 25%, by weight of the composition.

Sodium bicarbonate is known in the art for its use as an odor absorber. An example of sodium bicarbonate and its use as an underarm deodorant is found in U.S. Pat. No. 4,382,079, to Marschner, issued May 3, 1983, which is incorporated herein in its entirety by reference. When included in the present invention, sodium bicarbonate may be present from about 0.1% to about 50%, by weight of the composition.

The antimicrobial agents of the present invention are selected from a group consisting of antibacterial agents, antifungal agents, and mixtures thereof. Antimicrobial agents help destroy and/or control the amount of bacteria and/or fungi present on the skin. Preferred antimicrobial agents are zinc phenolsulfonate, zinc oxide, triclosan, Zelec® AM by DuPont, zinc ricinoleate, zinc undecylenate, and mixtures thereof. More preferred are zinc phenolsulfonate, zinc oxide, and triclosan. Triclosan is available from Ciba-Geigy as Irgasan DP-300. Examples of antimicrobial agents useful in the present invention are found in the *Cosmetic Bench Reference*, 1994 Edition, page 10, which is incorporated herein by reference. When included in the present invention, the antimicrobials are at a level of from about 0.01% to about 25%. Preferably from about 0.1% to about 10%, by weight of the present composition.

When used on the underarms, antiperspirant ingredients may be included in the present invention. Examples of antiperspirants known in the art are found in the *Cosmetic Bench Reference*, 1994 Edition, page 13, which is incorporated herein by reference. When included in the present invention, antiperspirants may be present from about 0.1% to about 25%, by weight of the composition.

Skin Aids

The compositions of the present invention also optionally include skin aids. The term "skin aids", as used herein, refers to skin protectants, emollients, and moisturizers.

Skin protectants useful in the present invention are found in the *Cosmetic Bench Reference*, 1994 Edition, page 53; and the Monograph on Skin Protectant Drug Products for Over-the-Counter Human Use, 21 CFR 347. Preferred skin protectants are corn starch, kaolin, mineral oil, sodium bicarbonate, dimethicone, zinc oxide, colloidal oatmeal, and mixtures thereof. When present, the skin protectants comprise from about 0.1% to about 80%, preferably from about 0.1% to about 30%, most preferably from about 0.1% to about 10%, by weight of the composition.

Emollients and moisturizers useful in the present invention can be found in the *Cosmetic Bench Reference*, 1994 Edition, pages 27–32 and 46–48, incorporated herein by reference. Preferred emollients and moisturizers are tocopherol, tocopheryl acetate, aloe, vegetable oils, mineral oil, petrolatum, jojoba oil, and mixtures thereof. More preferred are encapsulated or spray/freeze dried emollients. The use of spray/freeze dried or encapsulated emollients keeps the emollients protected in the powder carrier until they are released through shearing (such as rubbing against undergarments or clothes) or through contact with skin moisture. Examples of preferred commercial spray/freeze dried aloe useful in the present invention are Terra-Dry™ Freeze Dried Aloe, Terra-Pure™ Freeze or Spray Dried Aloe, and Terra-Spray™ Spray Dried Aloe, all from Terry Laboratories. When present, the skin aids comprise from about 0.1% to about 50%, preferably from about 0.1% to about 25%, most preferably from about 0.1% to about 10%, by weight of the composition.

Slip Compounds

The present compositions may optionally comprise slip compounds. The term "slip compounds", as used herein, refers to compounds which have unique structures which provide enhanced slip/lubrication characteristics of powders and/or reduced skin to skin friction between intertriginous skin sites.

Slip compounds of the present invention include polyethylene; nylon; polytetrafluoroethylene; silica which is in the form of microspheres, ellipsoids, barrel-shapes, and the like; mica, silicone (e.g. dimethicone) and metallic stearates (e.g. zinc stearate); and mixtures thereof. Preferred slip compounds are silicas which are in the form of microspheres, ellipsoids, barrel-shapes, and the like. Silica ellipsoids useful in the present invention are available from DuPont as ZELEC® Sil. Silica microspheres are available from KOBO as MSS-500, MSS 500/3, MSS-500/H, MSS-500/3H, MSS-500/N, and MSS-500/3N. Additionally, it is preferred that some of the silica of the present invention be fumed silica for increased flowability of the powder in addition to enhancing the slip characteristics. Fumed silica is available from Cabot Corporation (Cab-O-Sil®) and from Degussa (Aerosil®).

When present in the compositions of the invention, the slip compounds comprise from about 0.1% to about 35%, preferably from about 1% to about 10%, by weight of the composition.

Binders

The present invention may optionally also include dry or wet binders to help promote adhesion of the powder and active ingredients to the skin. Binders useful in the present invention are found in the *Cosmetic Bench Reference*, 1994 Edition, pages 13–14, which is incorporated herein by reference. Preferred binders calcium stearate, zinc stearate, isopropyl myristate, magnesium myristate, silicone, and mixtures thereof. More preferred are zinc stearate, dimethicone, and mixtures thereof.

When included in the composition, the binders are at a level of from about 0.1% to about 25%, preferably from about 1% to about 15%, by weight of the composition.

Anti-Pruritic Agents

Anti-pruritic agents such as those known in the art may be included in the compositions of the present invention. Examples of anti-pruritic agents useful in the present invention are Magnesium-L-Lactate, hydrocortisone, hydrocortisone acetate, and colloidal oatmeal. A description of anti-pruritic agents are found in the *Handbook of Non Prescription Drugs*, 10th Edition, p. 529, 1993; which is incorporated herein by reference. When included in the composition, anti-pruritic agents may be present from about 0.1% to about 40%, by weight of the composition.

Colorants

Colorants and dyes can be optionally added to the odor absorbing compositions for visual appeal and performance impression. Colorants suitable for use in the present invention are found in the *Cosmetic Bench Reference*, 1994 Edition, pages 21–22, which is incorporated herein by reference.

PROCESS OF MAKING COMPOSITIONS

The compositions of the present invention are prepared by the following steps: creating a mixture by mixing cyclodextrin and optional ingredients in a powder carrier via a commercially available mixer such as a vee-blender, double cone blender, or ribbon blender until the mixture is uniform; and creating a reduced size mixture using a commercially available size reduction technique such as hammer milling, impact milling, ball milling, or fluid energy milling until the desired particle size distribution is achieved.

Since the compositions of the present invention are to be applied directly to the skin or hair, various applicators are useful for delivering the compositions to the entire body for maximum odor control. For example, the compositions are preferably deposited in a bottle, a canister, a spray dispenser, a manually activated spray dispenser, or on a wipe structure which later is contacted with the skin to transfer the composition to the skin.

Bottles and canisters known in the art are suitable for use in delivering the compositions of the present invention. Bottles and canisters preferably comprise lids with small apertures for convenient dispensing of the composition.

The composition of the present invention can also be delivered as a suspended solution via a spray dispenser or a bottle, such that when applied or sprayed onto the skin, the solvent would immediately dry/volatilize off to leave a powder film. Examples of such suspension forms are aerosols, liquid powder suspensions, or silicone suspensions. When present in an aerosol composition, the powders of the present invention will usually be present in the range of from about 0.1% to about 15%, by weight of the composition. The incorporation of a powder into an aerosol is more fully explained in U.S. Pat. No. 4,078,051, to Pomot et al., issued Mar. 7, 1978; which is incorporated herein by reference in its entirety. This method is not preferred however for use on sensitive areas of the body such as the panty-area or other occluded skin areas since skin irritations may result from propellants commonly used in aerosol containers.

Preferred is a manually activated spray dispenser which delivers the composition as a powder without the use of propellants, and without the composition being in a solution form. Spray dispensers useful in the present invention are described more fully in U.S. Pat. No. 2,450,205, to Rose, issued Sep. 28, 1948; and U.S. Pat. No. 2,840,277, to Bach, issued Jun. 24, 1958, both of which are incorporated herein by reference in their entireties.

Any wipe structures and/or methods of making the wipe structures commonly known in the art may be used in the present invention. The wipe comprises a flexible dispensing means. The term "flexible dispensing means", as used herein, includes papers, cloths, non-wovens, films, foams, sponges, rollers, pads, tissues, cotton balls, and the like. Preferred wipe substrates comprise a porous material, such as the non-woven substrates, foams, or sponges, which are capable of holding the composition within the pores of the substrates. Examples of cellulosic non-wovens particularly useful and economic in the present invention is described in U.S. Pat. No. 4,191,609, Trokhan, issued Mar. 4, 1980, which is incorporated herein by reference in its entirety.

Techniques for combining the wipe substrates with the composition of the present invention are well known in the art. Examples of common methods of combining the composition to the wipe substrate may involve coating, immersing, dipping, sprinkling, or spraying, the wipe substrate with the composition of the present invention. The composition of the present invention is added to the wipe substrate at a level sufficient to provide the desired odor control and/or other desired skin benefits of the present invention.

METHODS OF USE

The present invention also encompasses a method of reducing body odor on a human comprising the application of the compositions described herein to skin. The present invention also encompasses a method of reducing vaginal odor on a human comprising applying the compositions described herein onto a pelvic region, external vagina, and/or panty-area. However, the compositions of the present invention should not be inserted into the vagina, nor applied onto the vulva.

An "effective amount" of the compositions of the present invention, as used herein, means an amount sufficient to absorb body odor to the point that it is not discernible by the human sense of smell.

The compositions of the present invention are topically applied directly to the skin or hair. The compositions can be delivered by placing the composition into a dispensing means and applying an effective amount via spraying, sprinkling, shaking, or rubbing the composition onto the desired skin surface; typically the entire body. Preferably the dispensing means is a sprinkling canister, a spray bottle, or a pre-formed wipe which comprises a flexible dispensing means.

Alternatively, the user may deposit the composition of the present invention onto a wipe comprising a flexible dispensing means of his or her own choosing. To do this, the user simply chooses a flexible dispensing means such as a washcloth or puff; transfers the composition of the present invention from a bottle or other suitable container over the chosen flexible dispensing means; and applies the composition to the desired area of the body. The user may also use his/her hand to apply the compositions of the present invention. The user may use as much or as little of the composition of the present invention as he/she desires, depending upon their intended use and degree of odor control necessary.

The following non-limiting examples illustrate the formulations and methods of use of the present invention.

EXAMPLE I

| Ingredient | % W/W |
| --- | --- |
| Corn Starch (Topical Starch) | 64.80 |
| Silica (Microspheres) | 2.00 |
| Fumed Silica | 2.00 |
| Zinc Phenolsulfonate | 3.00 |
| Triclosan | 0.20 |
| Cyclodextrin | 3.00 |
| Aloe Vera, Freeze/Spray Dried | 1.00 |
| Nylon-12 | 5.00 |
| Zinc Stearate | 7.00 |
| Tocopheryl Acetate Microcapsules | 2.00 |
| Dimethicone | 10.00 |
| Total | 100.00 |

Example I may also comprise a colorant.

EXAMPLE II

| Ingredient | % W/W |
| --- | --- |
| Corn Starch (Topical Starch) | 52.20 |
| Talc | 10.00 |
| Silica (Microspheres) | 3.00 |
| Fumed Silica | 1.00 |
| Zinc Phenolsulfonate | 3.00 |
| Triclosan | 0.30 |
| Cyclodextrin | 13.00 |
| Aloe Vera, Freeze/Spray Dried | 0.50 |

-continued

| Ingredient | % W/W |
|---|---|
| Nylon-12 | 5.00 |
| Zinc Stearate | 3.00 |
| Tocopheryl Acetate Microcapsules | 2.00 |
| Mineral Oil | 2.00 |
| Dimethicone | 5.00 |
| Total | 100.00 |

Example II may also comprise an anti-pruritic agent such as Magnesium-L-Lactate.

EXAMPLE III

| Ingredient | % W/W |
|---|---|
| Rice Starch | 54.50 |
| Mica | 2.00 |
| Silica (Ellipsoids) | 2.00 |
| Fumed Silica | 1.00 |
| Triclosan | 0.50 |
| Aluminum Chlorohydrate | 5.00 |
| Cyclodextrin | 6.00 |
| Aloe Vera, Freeze/Spray Dried | 1.00 |
| Polyethylene Powder | 5.00 |
| Zinc Stearate | 5.00 |
| Tocopheryl Acetate Oil (Vit. E Acetate) | 3.00 |
| Dimethicone | 10.00 |
| Nylon N-12 | 5.00 |
| Total | 100.00 |

Example III may also comprise a zeolite.

EXAMPLE IV

| Ingredient | % W/W |
|---|---|
| Aluminum Starch Octenyl Succinate (Dry Flo ® Pure) | 30.80 |
| Silica (Ellipsoids) | 4.00 |
| Zinc Phenolsulfonate | 7.00 |
| Triclosan | 0.60 |
| Cyclodextrin | 10.00 |
| Aloe Vera Gel/Oil | 1.00 |
| Zeolite | 10.00 |
| Talc | 13.60 |
| Polyethylene Powder | 7.00 |
| Zinc Stearate | 5.00 |
| Mineral Oil | 5.00 |
| Dimethicone | 6.00 |
| Total | 100.00 |

EXAMPLE V

| Ingredient | % W/W |
|---|---|
| Tapioca Starch | 54.60 |
| Talc | 4.90 |
| Silica (Microspheres) | 2.50 |
| Fumed Silica | 2.00 |
| Zinc Oxide | 4.00 |
| Triclosan | 1.00 |
| Cyclodextrin | 4.00 |
| Aloe Vera Gel/Oil | 2.00 |
| Nylon-12 | 10.00 |
| Zinc Stearate | 6.00 |

-continued

| Ingredient | % W/W |
|---|---|
| Isopropyl Myristate | 4.00 |
| Dimethicone | 5.00 |
| Total | 100.00 |

Example V may also comprise sodium bicarbonate.

EXAMPLE VI

| Ingredient | % W/W |
|---|---|
| Corn Starch (Topical Starch) | 29.25 |
| Oat Flour/Colloidal Oatmeal | 16.35 |
| Silica (Microspheres) | 2.50 |
| Silica (Ellipsoids) | 1.50 |
| Kaolin | 8.00 |
| Zinc Oxide | 2.00 |
| Triclosan | 0.40 |
| Cyclodextrin | 5.00 |
| Aloe Vera Gel/Oil | 2.00 |
| Nylon-12 | 4.00 |
| Polyethylene Powder | 4.00 |
| Zinc Stearate | 10.00 |
| Tocopheryl Acetate Microcapsules | 5.00 |
| Dimethicone | 10.00 |
| Total | 100.00 |

EXAMPLE VII

| Ingredient | % W/W |
|---|---|
| Corn Starch (Topical Starch) | 50.80 |
| Kaolin | 14.50 |
| Silica (Microspheres) | 2.50 |
| Silica (Ellipsoids) | 1.50 |
| Fumed Silica | 0.50 |
| Zinc Phenolsulfonate | 2.00 |
| Triclosan | 0.20 |
| Cyclodextrin | 8.00 |
| Aloe Vera Gel/Oil | 3.00 |
| Nylon-12 | 2.00 |
| Polyethylene Powder | 5.00 |
| Tocopheryl Acetate Microcapsules | 3.00 |
| Isopropyl Myristate | 2.00 |
| Dimethicone | 5.00 |
| Total | 100.00 |

Prepare the above Examples by the following steps: create a mixture by mixing cyclodextrin, dry ingredients, and a powder carrier in a commercially available mixer such as a vee-blender, double cone blender, or ribbon blender until the mixture is uniform; reduce the particle size of the mixture using a grinding/pulverizing technique such as hammer milling, impact milling, ball milling, or fluid energy milling; and create a second mixture by adding any liquid phase emollients, moisturizers, and/or skin protectants to the mixture, preferably using spray atomization while mixing for a more even dispersion. The second mixture can then undergo a second pulverizing/grinding step, and if desired, an air classifying operation.

Preparation for Application to Skin

The compositions of the present invention, such as those formed from the examples may be loaded onto a wipe or deposited into a spray device or canister. The compositions may be applied directly onto the skin or onto a flexible dispensing means of the user's choosing for convenient application to the skin.

To prepare wipes: Coat, sprinkle, or spray the composition onto a dry flexible dispensing means until desired coating or thickness of composition on the flexible dispensing means is achieved.

To prepare spray: Deposit the composition into the selected spray package. Close the package for storage until consumer use. To prepare a pressurized aerosol spray, transfer the composition into a suitable container. Pressurize and seal the container after injection of propellant materials.

EXAMPLE VIII

A woman with stress urinary incontinence finds that the wetness associated with this condition causes vaginal odor which she wants to remove from the skin and control. After urinating, the woman wipes her external vagina and pelvic region with a wipe containing the composition in Example 1. This woman notices less odor after using the wipe.

EXAMPLE IX

A large-breasted woman finds that when she exercises, she tends to experience sweating and skin chafing under the breasts. Before and after exercising, she applies the composition from Example IV via a manual spray bottle. She sprays the composition under her breasts and the composition provides odor protection against odorous compounds that are exuded with sweat and/or sweat decomposition. This woman notices less odor and feels more comfortable after using the powder spray.

EXAMPLE X

A man has severe allergies to cosmetic deodorants and antiperspirants and avoids using such products. This results in uncontrolled and embarrassing body odor. His doctor suggests applying the mild odor absorbing composition of Example VI after showering. The man applies the composition to his entire body via a spray each morning after showering, and suffers no allergic reaction. The man feels comfortable without the embarrassment of lingering, uncontrollable body odor. The man keeps a pouch of wipes at work, which also contain the composition of Example VI, for convenient and discrete reapplication as needed, particularly on hot and sweaty days.

What is claimed is:

1. An odor absorbing composition comprising:
   a. from about 0.1% to about 25%, by weight of the composition, of uncomplexed cyclodextrin; and
   b. a powder carrier;

and wherein said composition is safe for use on human skin.

2. The composition of claim 1 wherein the cyclodextrin is selected from the group consisting of beta-cyclodextrins, derivatives of beta-cyclodextrins, alpha-cyclodextrins, derivatives of alpha-cyclodextrins, gamma-cyclodextrins, derivatives of gamma-cyclodextrins, and mixtures thereof.

3. The composition of claim 2 wherein the cyclodextrin is beta cyclodextrin, hydroxypropyl alpha-cyclodextrin, hydroxypropyl beta-cyclodextrin, methylated-alpha-cyclodextrin or methylated-beta-cyclodextrin, and mixtures thereof.

4. The composition according to claim 1 wherein particle sizes are from about 1 micron to about 100 microns.

5. The composition according to claim 1 wherein particle sizes are from about 1 micron to about 60 microns.

6. The composition according to claim 1 wherein particle sizes are from about 1 micron to about 20 microns.

7. The composition according to claim 4 wherein particle sizes of the cyclodextrin from about 1 micron to about 12 microns.

8. The composition according to claim 6 wherein particle sizes of the cyclodextrin are from about 1 micron to about 5 microns.

9. The composition of claim 1 further comprising adjunct odor controlling agents selected from the group consisting of zeolites, activated charcoal, sodium bicarbonate, antimicrobial agents, and antiperspirants.

10. The composition of claim 1 further comprising skin aids selected from the group consisting of skin protectants, emollients, and moisturizers.

11. The composition of claim 1 further comprising slip compounds.

12. The composition of claim 4, delivered as a powder, by a manually activated spray dispenser.

13. A composition according to claim 1 wherein the composition of claim 1 is deposited on a wipe which comprises a flexible dispensing means.

14. A method of reducing body odor on a human comprising the application onto skin of a composition comprising:
    a. from about 0.1% to about 25%, by weight of the composition, of uncomplexed cyclodextrin; and
    b. a powder carrier.

15. A method according to claim 14, wherein the body odor is vaginal odor, comprising the application of the composition onto a pelvic region, and external vagina, and/or a panty-area.

16. A process for making an odor absorbing composition comprising the steps of:
    a. making a mixture of powder carrier and cyclodextrin by mixing the powder carrier and the cyclodextrin in a commercially available mixer until uniform; and
    b. creating a reduced size mixture using a commercially available size reduction technique until the desired particle size distribution is achieved.

* * * * *